United States Patent [19]

Pologe

[11] Patent Number: 5,335,659
[45] Date of Patent: Aug. 9, 1994

[54] NASAL SEPTUM PROBE FOR PHOTOPLETHYSMOGRAPHIC MEASUREMENTS

[75] Inventor: Jonas A. Pologe, Boulder, Colo.

[73] Assignee: Ohmeda Inc., Liberty Corner, N.J.

[21] Appl. No.: 45,952

[22] Filed: Apr. 12, 1993

[51] Int. Cl.$^5$ ................................................. A61B 5/02
[52] U.S. Cl. ...................................... 128/633; 128/664; 128/207.18
[58] Field of Search ............... 128/664, 665, 666, 721, 128/719, 633, 207.18, 637, 667, 671, 634

[56] References Cited

U.S. PATENT DOCUMENTS

| | | | |
|---|---|---|---|
| 3,359,975 | 12/1967 | Sherman | 128/666 |
| 3,810,460 | 5/1974 | Van Nie | 128/666 |
| 4,334,544 | 6/1982 | Hill et al. | 128/666 X |
| 4,800,495 | 1/1989 | Smith | 128/664 |
| 5,086,229 | 2/1992 | Rosenthal et al. | 128/633 X |
| 5,113,857 | 5/1992 | Dickerman et al. | 128/207.18 |

*Primary Examiner*—Richard J. Apley
*Assistant Examiner*—John Mulcahy
*Attorney, Agent, or Firm*—Roger M. Rathbun; Larry R. Cassett; James M. Graziano

[57] ABSTRACT

The nasal septum probe of the present invention mounts the optical devices of a photoplethysmographic probe in a housing that clips onto the patient's nasal septum. The septum provides an arterial bed for monitoring purposes and this locus is not subject to significant patient motion or peripheral shutdown of arteriolar blood flow. Furthermore, one embodiment of the invention shows a combination of the photoplethysmographic apparatus with a nasal cannula to provide dual purpose apparatus to minimize the sensor and cable proliferation.

6 Claims, 3 Drawing Sheets

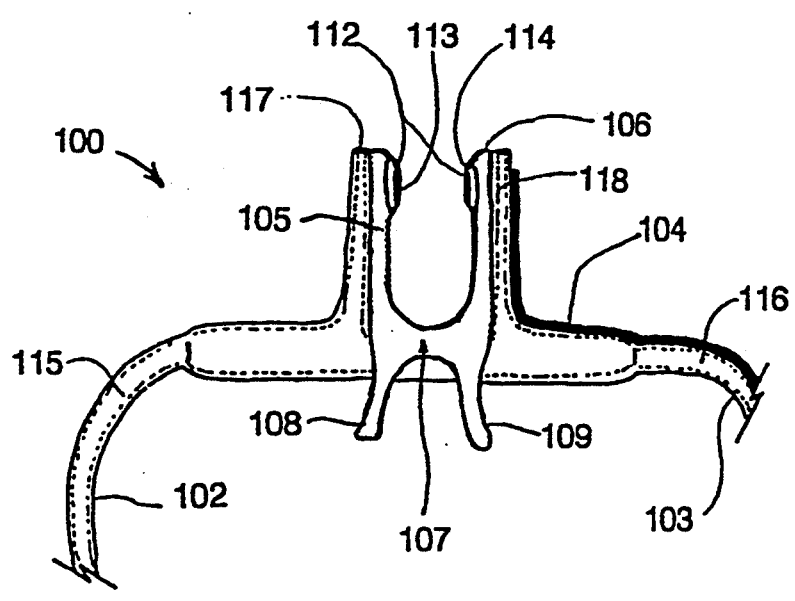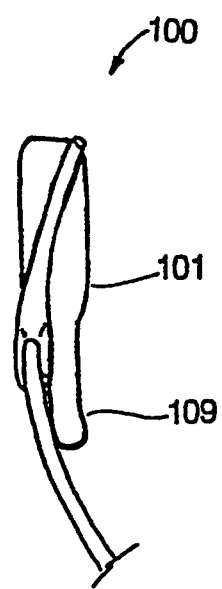
Figure 1                    Figure 2

NASAL SEPTUM PROBE FOR PHOTOPLETHYSMOGRAPHIC MEASUREMENTS

FIELD OF THE INVENTION

This invention relates to medical monitoring apparatus and, in particular, to a nasal septum probe for photoplethysmographic measurement of components of arterial blood.

PROBLEM

It is a problem in the field of medical monitoring apparatus to non-invasively monitor the arterial blood of a patient using a simple probe. It is difficult to produce a probe that is simple to use and yet provides accurate measurements. Existing probes typically consist of sensors that are attached to a conformable pad, which pad is equipped with adhesive material or velcro material to allow the sensors to be applied to a patient's finger and secured thereon. The conformable pad is configured so that it is adjustable to compensate for variations in the size and topology of the patient's finger. Difficulties with this type of probe include the fact that the fingers are subject to a loss of perfusion in a cold or shock subject, making measurement difficult or impossible. Accessibility to fingers can also be a problem. This occurs in the operating room when the arms are under drapes, and can occur in certain injury conditions, such as burns or crushing injury. Furthermore, the use of the conformable pad on the patient's finger may be in conjunction with numerous other pieces of monitoring equipment, causing a proliferation of wires and sensors attached to the patient. This proliferation of wires and sensors decreases the patient's mobility and increases the possibility that this equipment will interfere with each other. Therefore, there is a need for a simple, reliable, alternate site probe apparatus for medical monitoring purposes.

U.S. Pat. No. 4,800,495 discloses a method and apparatus for processing signals used in oximetry. This patent notes the nasal septum as a desirable site for performing photoplethysmographic measurements since it is highly vascularized and a useable amount of light can be passed through this tissue. The required characteristics of a probe that can be used are listed as: the sensor must maintain its position in spite of patient movement, the sensor should apply only insubstantial pressure to the site, the sensor should be quickly attachable to the patient. However, no probe specifically designed for the nasal septum site is disclosed in this patent.

SOLUTION

The above described problems are solved and a technical advance achieved in the field by the nasal septum probe of the present invention which non-invasively and unobtrusively provides a photoplethysmographic arterial blood monitoring capability. Photoplethysmographic techniques are used to perform a number of different medical monitoring functions. One such monitoring application is the field of pulse oximetry, wherein the oxygen saturation of the patient's arterial blood in a patient's extremity, such as a finger, is non-invasively measured using photo-optical techniques. A difficulty with pulse oximetry is that the small pulsatile component of the transmitted light, due to the pulsatile nature of the arterial flow, must be accurately measured to determine the oxygenation of the hemoglobin contained in the arterial blood. These measurements are highly susceptible to motion artifacts caused by the shifting of the probe on the patient. It is obvious that placing the probe on a patient's extremity, such as a finger, subjects the probe to a significant amount of patient movement. It is advantageous therefore to mount the probe in a location on the patient where there is an adequate source of arterial blood and which location is not subjected to significant patient movement. The nasal septum probe of the present invention mounts the optical devices of a photoplethysmographic probe in a housing that clips onto the patient's nasal septum. The nasal septum provides an arterial bed for monitoring purposes and this locus is not subject to significant patient motion. In addition, the nasal septum blood supply is from the internal carotid artery and it is therefore not affected by peripheral shutdown, and considerably less susceptible to low perfusion. Furthermore, one embodiment of the invention shows a combination of the photoplethysmographic probe apparatus with a nasal cannula to supply oxygen to the patient, thereby providing a dual purpose apparatus to minimize probe proliferation.

BRIEF DESCRIPTION OF THE DRAWING

FIG. 1 illustrates a front view of the nasal septum probe of the present invention;

FIG. 2 illustrates a side view of the nasal septum probe;

DETAILED DESCRIPTION

Medical monitoring equipment makes use of photoplethysmographic techniques to non-invasively monitor characteristics of the patient's circulatory system. One specific instance of medical monitoring equipment is the pulse oximeter system which measures the oxygen saturation of the hemoglobin in the arterial blood by means of photoplethysmographic techniques. To accomplish this, a pair of light emitting diodes are juxtaposed to a site on the patient that is rich in arterial blood. A light detector is placed on the opposite side of the arterial bed to measure the intensity of the light that is transmitted through the arterial bed. The light sources produce a plurality of beams of light at predefined wavelengths, each of which is selected to be highly absorbed by a component in the arterial blood that is to be measured. The light detector(s) measure the magnitude of the plurality of beams of light that are transmitted through the arterial bed. Since the pulsatile component of the arterial flow is being measured, the incremental change in the magnitude of the transmitted light is indicative of the pulsatile component of the arterial flow. The light sources and detector(s) are preferably mounted on opposite sides of an arterial bed, and a patient's finger is typically used as the site to mount the sensors. This locus is, however, subject to significant motion, low perfusion states, and suffers from the disadvantage of being extremely variable in size and shape. Furthermore, the fingers are often inaccessible to the clinician and it can be difficult to route the signal conductors to the pulse oximeter apparatus in a manner that will not be subject to entanglement by patient movement.

Nasal Septum Probe Architecture

Figures 3, 4:
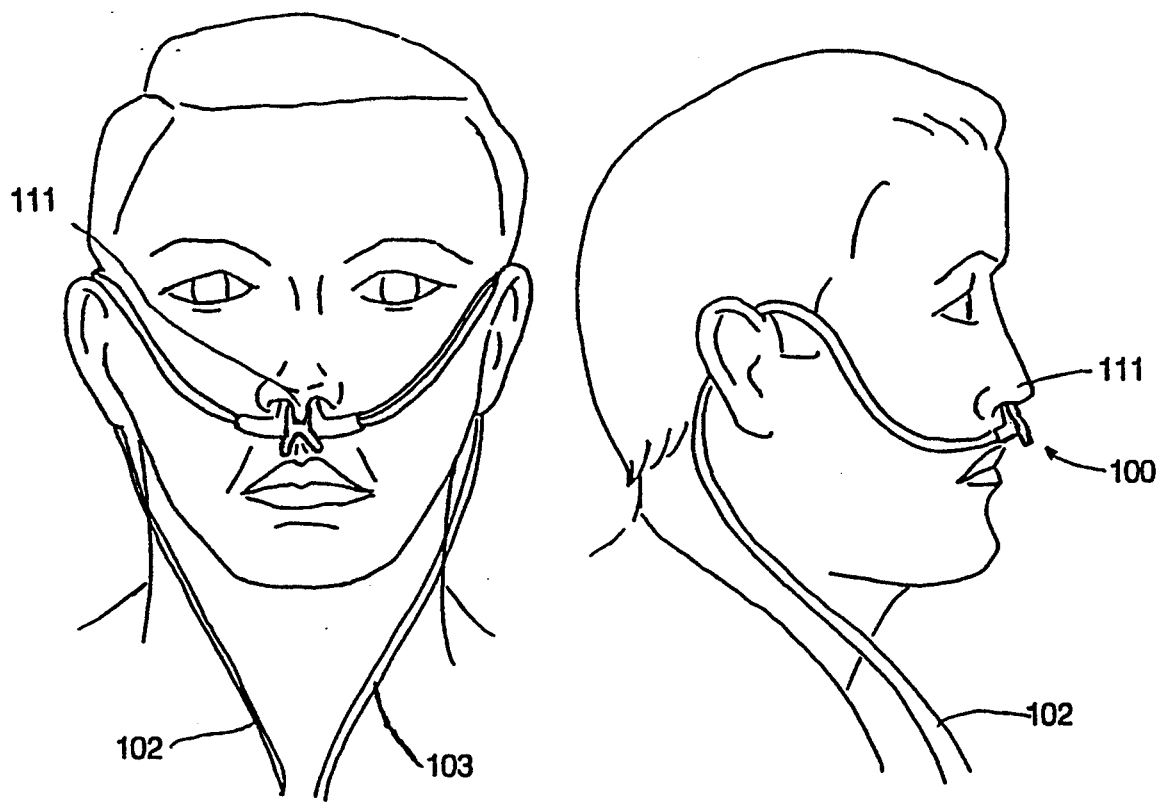
FIG. 3 illustrates a front view of the nasal septum probe in use on a patient.
FIG. 4 illustrates a side view of the nasal septum probe in use on a patient.

The nasal septum probe 100 of the present invention is illustrated in front view in FIG. 1, side view in FIG. 2 and in use on a patient in front view in FIG. 3 and in side view in FIG. 4. An alternative embodiment is shown in front view in FIG. 5 and side view in FIG. 6. The nasal septum probe 100 provides a simple sensor system for use in photoplethysmographic monitoring of the patient's circulatory system. The nasal septum probe 100 consists of a housing 101 that is clipped to the patient's nasal septum 111 and signal conductors 104. One or more supports 102,103 may be present to assist in maintaining the nasal septum probe 100 in place on the patient. The supports 102,103 can be comprised of the signal conductors 104 or the signal conductors 104 can be incorporated into the support 103 to form a substantially unitary structure. The nasal septum probe 100 is comprised of a clip type structure consisting of a body 107 having a pair of parallel oriented spaced apart probe arms 105,106 that are flexibly mounted to the body 107 and which function to securely fasten the nasal septum probe 100 to the patient's nasal septum 111. Additionally, a pair of extensions 108,109 could also be included as extensions of the probe arms 105,106 or separate structures also directly connected to the probe body, oriented in a parallel spaced apart configuration, extending in an opposite direction from the probe arms 105,106 to enable the user to insert the nasal septum probe 100 on the nasal septum 111 of the patient. This is accomplished by the user squeezing the two extensions 108,109 together, thereby causing the body 107 to flex in a response to the displacement of the extensions 108,109 and causing the two probe arms 105,106 to separate further apart from each other. The two probe arms 105,106 can then be inserted one on either side of the patient's nasal septum 111 and the extensions 108,109 released to apply the probe 100 to the nasal septum 111. The release of the extensions 108,109 permits the flexible body 107 to return to its original shape thereby causing the two probe arms 105,106 to move together a sufficient distance to securely grasp the patient's nasal septum 111 between the two probe arms 105,106.

To measure any given blood analyte in arterial blood, the concentration of dominant absorbers contained in the arterial blood must be measured. In the case of pulse oximetry, the concentration (or at best the ratio) of the oxygenated and deoxygenated hemoglobin components of the arterial blood must be measured. In order to accomplish this, one of the plurality light emitting devices in light source 113 is selected to produce a beam of light at approximately 660 nm, which wavelength is more strongly absorbed by deoxygenated hemoglobin that by oxyhemoglobin. A second light emitting device in source 113 is selected to produce a beam of light at approximately 940 nm where the oxygenated hemoglobin is the more absorbing of the two species. The analog data signals produced by light detector 114 in response to the received beams of light are transmitted from probe 100 over conductors 104 to the pulse oximeter instrument (not shown). An exactly analogous system with additional light sources (or different light sources), and perhaps different detector apparatus, would be used to measure other blood anolytes (such as total hemoglobin, carboxyhemoglobin, etc.).

The dimensions and configuration of the two probe arms 105,106 are such that they place the light source 113 and detector(s) 114 in position on either side of the patient's nasal septum 111 to illuminate the arterial bed that is contained therein. Lenses 112 cover and electrically insulate the light sources and detectors from the patient. It is preferable that the probe arms 105,106 be implemented in a shape that substantially conforms to the contours of the patient's nasal septum 111 to minimize irritation of the nasal septum 111 when the probe 100 is in place. Similarly, the extensions 108,109 should be configured to provide a surface that is easily gripped by the user and of sufficiently small dimensions to not be susceptible to interference or of sufficient mass to have a tendency to pull the nasal septum probe 100 loose.

Supports

The embodiment illustrated in FIG. 1 also shows the use of a pair of supports 102,103 comprising an elongated flexible material that can be tubular in shape. These supports are connected each at one end to a corresponding side of the body 107 of the probe 100. One or both of the supports 102,103 can include signal conductors 104 from the light sources 113 and detectors 114 to carry the signals from these elements to a connector (not shown) that is mounted at the other end of the supports 102,103. A moveable collar (not shown) can be provided to enable the user to adjust the supports 102,103 when the probe 100 is in use on a patient. The collar slides in a frictional manner along the length of the two supports 102,103 to enlarge or reduce the size of the loop that is created by the two supports 102,103 that exit either side of the probe body 107 and would be configured to loop around the patient's head to provide additional support to maintain the probe 100 in place on the patient's nasal septum 111.

Nasal Septum Probe Combined with Nasal Cannula

An alternative embodiment of the nasal septum probe 100 incorporates a nasal cannula as an integral part of its structure. In this embodiment, one or both of the supports 102,103 includes an air passage 115,116 to provide a supply of oxygen to the patient via the probe body 107 and arms 102,103 which again would be tubular and having an air passage 117,118 that is integral thereto along its length. The supports 102,103 would therefore provide oxygen through the body 107 and probe arms 105,106 of the nasal septum probe 100 while also providing a mounting for the light sources 113 and detector(s) 114 and their associated signal cables 104 for medical instrumentation, such as a pulse oximeter instrument. Alternatively, the air passages 115,116 can be a separate tubular structure mounted on probe arms 105,106 as shown in FIGS. 1 and 2. The integration of these two pieces of equipment provides a natural synergy since the oxygen saturation of a patient's hemoglobin when the patient is provided with an oxygen supply is of significant interest to the medical staff. This combination of elements provides significant enhancement over the existing apparatus wherein only a single probe is used to provide both the oxygen supply and oxygen saturation measurement functions, rather than two diverse elements that are presently in use. The reduction in the number of elements attached to the patient simplifies the management of the oxygen administration and patient monitoring tasks and also improves the patient's mobility while avoiding the use of a probe attached to the patient's appendage.

Alternate Embodiment

Figure 5:
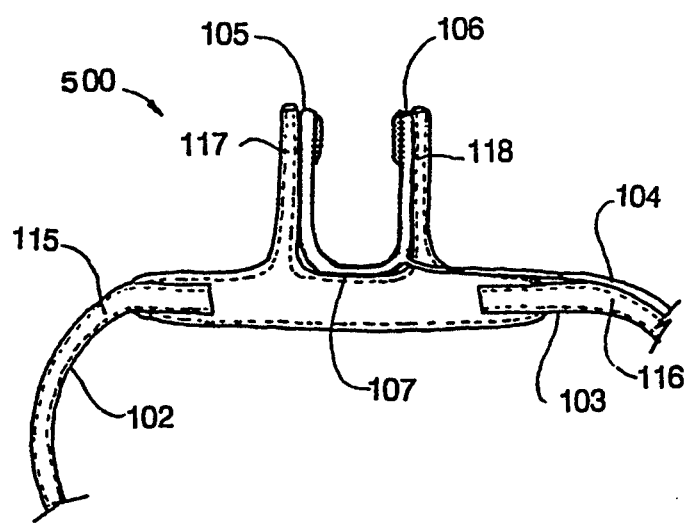
FIG. 5 illustrates a front view of an alternative embodiment of the nasal septum probe combined with a nasal cannula.
Figure 6:
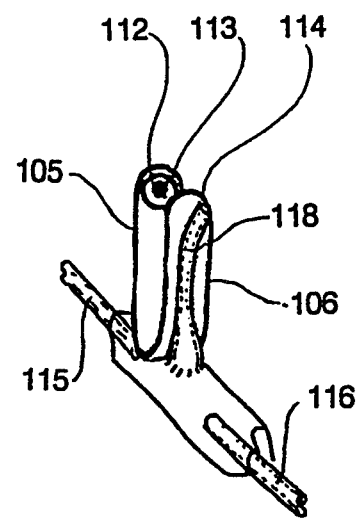
FIG. 6 illustrates a side view of the alternate embodiment of the nasal septum probe.

Another embodiment of the nasal septum probe 500 is illustrated in front view in FIG. 5 and side view in FIG. 6. This embodiment makes use of a U-shaped housing that dispenses with the use of extensions 108,109. The probe arms 105,106 extend in parallel oriented spaced apart relationship in parallel with the optional nasal cannula air passages 117,118. The light sources 113 and detector(s) 114 are mounted on the probe arms 105,106. The supports 102,103 and remaining attributes of the nasal septum probe 500 are similar to the structure disclosed in FIGS. 1-4.

It is expressly understood that the claimed invention is not to be limited to the description of the preferred embodiment but encompasses other modifications and alterations within the scope and spirit of the inventive concept.

I claim:

1. A probe for releasably attaching to the nasal septum of a patient to perform multi-wavelength photoplethysmographic measurements of the arterial blood flow in said nasal septum, comprising:

probe body;

first probe arm extending outward from a surface of said probe body and of dimensions to be insertable into a patient's nostril;

second probe arm extending outward from said surface of said probe body in a parallel spaced apart relationship with said first probe arm and of dimensions to be insertable into a patient's nostril;

first and second support means attached to said probe body for securing said probe in place on said nasal septum, wherein at least one of said first support means and said second support means is hollow and connected at a first end to a one of said first and second probe arms and connectable at a second end thereof to a supply of gas for transporting said gas from said supply to said nasal septum;

at least two light sources mounted at the distal end of said first probe arm on an interior surface thereof;

light detector mounted at the distal end of said second probe arm on an interior surface thereof;

wherein said interior surface of both said first and said second probe arms face each other to place both said at least two light sources and said light detector in contact with said nasal septum on opposite sides thereof at a vascularized site on said nasal septum, when said nasal septum is positioned between said first and said second probe arms, to enable light beams produced by said at least two light sources to pass through said vascularized site on said nasal septum before being received by said light detector to perform photoplethysmographic measurements on the arterial blood flowing through said vascularized site on said nasal septum.

2. The probe of claim 1 wherein said first probe arm and said second probe arm are deformably attached to said probe body for compliantly conforming to said nasal septum when said first probe arm and said second probe arm are placed in contact with said nasal septum.

3. The probe of claim 1 further comprising:

first extension extending outward from said probe body; and second extension extending outward from said probe body in a parallel spaced apart relationship with said first extension, said first extension and said second extension operable to cause said first probe arm and said second probe arm to separate from each other when said first extension and said second extension are moved toward each other.

4. The probe of claim 1 wherein said first support means and said second support means comprise tubular elements attached to said probe body at one end and capable of being secured together to form a loop for securing said probe to said patient.

5. The probe of claim 1 further comprising:

means for electrically interconnecting said at least two light sources and said light detector with a medical monitoring instrument.

6. The probe of claim 1 further comprising:

means secured to at least one of said first hollow tube and said second hollow tube for electrically interconnecting said at least two light sources and said light detector with a medical monitoring instrument.

* * * * *